Dec. 19, 1972 H. A. JOHNSON, JR Plant Pat. 3,275
STRAWBERRY PLANT
Filed April 9, 1971
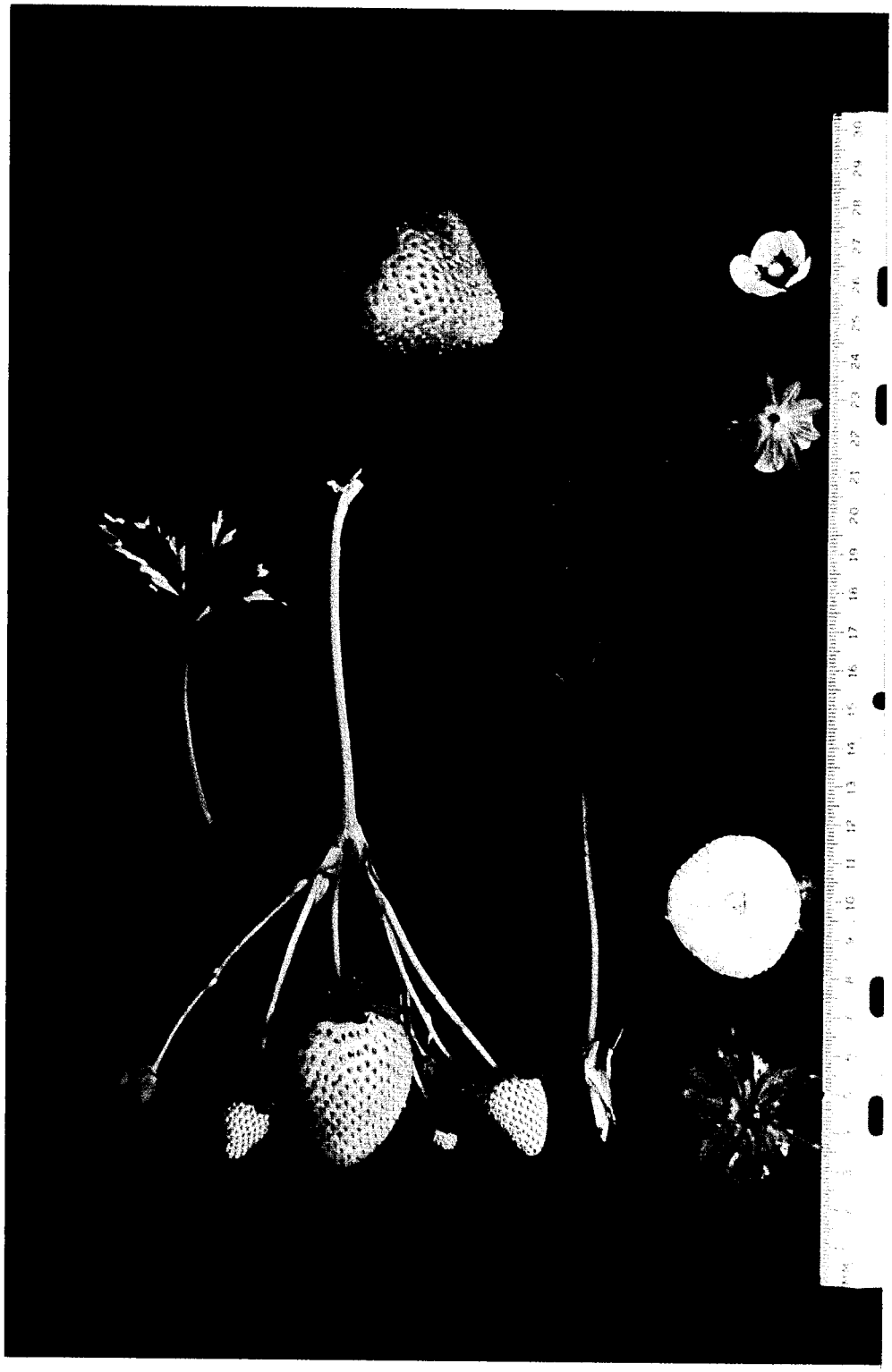
HAROLD A. JOHNSON, JR.
Townsend and Townsend United States Patent Office Plant Pat. 3,275
Patented Dec. 19, 1972

3,275
STRAWBERRY PLANT

Harold A. Johnson, Jr., Watsonville, Calif., assignor to Driscoll Strawberry Associates, Inc., Watsonville, Calif.

Filed Apr. 9, 1971, Ser. No. 132,920
Int. Cl. A01h 5/03
U.S. Cl. Plt.—49 1 Claim This invention relates to a new and distinct variety of strawberry plant which is the result of a cross of the unpatented variety known to The Strawberry Institute of California as Selection No. L44.1, and The Strawberry Institute of California Selection E2, Patent No. 2,611.

The seedlings resulting from the aforementioned cross were grown and asexually multiplied in Shasta County, Calif., and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

Plant parts of the new variety, typical in size, shape and color are pictured in the accompanying photograph. A berry in cross section illustrates flesh color and characteristic core cavity. The inflorescence pictured illustrates typical branching and relative size during the summer production period. The picture shows the presence of two secondary peduncles, the most common number, but there may be three present on a single inflorescence. The picture also illustrates a large calyx which has large serrated sepals that overlap each other. Pedicels and bracts on the inflorescence show a slight reddening which is typical of many inflorescences. The leaf is typical in appearance and size with the central leaflet illustrating the acute serrations present, plus the presence of small serrations between larger ones. The flower is also typical of primary or secondary flowers and petals during most of the year. The variegated leaf present is peculiar to this variety in that one plant in every several hundred plants often show this condition, referred to in strawberry literature as "streak." A plant with this "streak" condition will often show the variegated effect on all plant parts including the fruit. This trait is a valuable marker in the identification of the variety. This "streak" is not the progressive, degenerate, virus-like condition called June Yellows.

The novel plant is small to medium in size and vigorous when given ample cold storage before being planted during a winter planting. The transplant is medium in size as it comes from the nursery and produces a vigorous young plant early in the spring. A good crown crop is produced if ample nutrition plus cold storage is given the plant. It is a spring variety, but has the ability of uniform production during the first year after being planted. The variety does have the ability to produce more consistently, however, than the Goldsmith variety, Plant Patent No. 1,735, if given excessive chilling before planting or if excessive chilling temperatures are obtained after being planted. Subsequent crops after the crown crop are abundant with many inflorescences per plant coming continuously during the first and second year of production. Fruit size may drop off considerably however unless a strong plant is maintained. The plant does not grow as vigorously on sandy or weak sediment soils as on heavy loam or adobe soil types. If considerable chilling has been given the plant, either in storage or after being planted, abundant runners may be produced during the first year, but the plant has the ability to crop and produce runners at the same time. Cropping generally continues through late fall in the coastal regions of California.

The novel plant of the present invention is distinguished from other varieties by its flowers, fruit, and plant characteristics. The plant is generally smaller than the Goldsmith variety. The petioles may be equal to Goldsmith, but the leaflets are smaller and darker. This is especially true when the plant of the new variety is under stress while still in production when the plant parts become small and dark in color. The rugoseness, shape and outline of leaflets is equal to that of Goldsmith. The petiolule of the new variety is generally longer than that of Goldsmith and the serrations of leaflets are more abundant.

There are more inflorescences per plant on the new variety than Goldsmith. The crown crop is generally produced during late April with the main crop coming during late May. Individual inflorescences are generally equal to Goldsmith in length. The common peduncle of the new variety may be long or short, but is generally longer as the year progresses. The pedicel holding the primary berry originates mainly from the axil of secondary peduncles. The bracts found at axils formed from the union of pedicels and peduncles often have a red tinge. Pedicels also often have a reddish tinge near the point where they join the calyx. It is unusual for a primary berry on a given inflorescence not to ripen ahead of secondary berries.

The fruit of this new variety is unique in that it has a consistent uniform surface with very few irregularities. Pollen production is abundant with consistent fertilization of the seed. Ridging or malformation is the exception. The fruit is generally medium wedge to conic in outline as described in the U.S.D.A. Bulletin No. 1043. The epidermis is exceptionally firm and has a high gloss.

The seeds are abundant, uniformly spaced and generally exerted. During some periods of the year they are exerted to the extent that they may become detached from the fruit surface when fruit rub against fruit during transit. The flesh is firm with the exception of short periods during the early spring, and there is a small to medium cavity and core. The firmness of the fruit is generally considered firmer than that of Goldsmith enhancing the shelf life of this variety. Fertilization also takes place uniformly on tertiary and quaternary fruit often to the detriment of the variety as many of the quaternary berries become relatively small in size. Early primaries may equal Goldsmith in size, but the average fruit size of all berries is smaller than that of Goldsmith. The fruit surface color of the new variety is often darker than that of Goldsmith, but during some periods of the year the surface color away from the light may be lighter giving a mottled effect.

Individual flowers are showy and are obvious above the plant during most of the year. The calyx of this variety is considered large in proportion to the fruit size and is larger than that of Goldsmith. Individual sepals of primary and secondary berries are large and overlap each other and have an abundance of serrations.

The dessert quality of this new variety is good and is sweeter to the taste than the Goldsmith variety. There is generally no aroma peculiar to the flesh of this variety.

This new variety appears to be equally susceptible to the Two-Spotted Mite as the Goldsmith variety. It is quite tolerant to mildew. It has not been completely tested against Verticillium or the Red Stele diseases. As a seedling and selection, this variety withstood the natural invasion of certain virus components found in central California without losing its ability to produce.

The varietal characteristics of the novel plant, described below in detail, were observed mainly during the first fruiting season, but reference is also made to the appearance during the second fruiting year. Observations were made in the Watsonville area of California which is a cool coastal area near the Pacific Ocean. The color terminology is in accordance with Ridgeway's Color Standards and Nomenclature (1912 edition).

*Plants*

Small to medium, vigorous if given ample chilling before being planted, and has an extensive root system.

*Leaves*

Small to medium in size. Central leaflet is usually 5 to 7 cm. wide with the width often equal to or slightly greater than the length. Petioles vary in length depending on the time of year and the nutrition of the soil, but most petioles are relatively short 12 to 17 cm. from their base to the petiolules. Petiolules are mostly 7 to 10 mm. Bracts may be present on petioles but are not abundant. Leaflet serrations are abundant and acute. Small serrations may be present at union of margins of larger serrations. The color of the upper side of leaflets at Watsonville during late summer is Dark Cress Green, Plate No. XXXI. One plant in every several hundred shows leaves with variegation present (see illustration).

*Runners*

Runners are vigorous and abundant both at the nursery and in the fruiting beds with a characteristic reddish color present.

*Inflorescence*

Inflorescence is usually 20 to 25 cm. long depending on the time of year. Secondary peduncles are mainly two in number. Pedicel holding primary berries originate at the axil formed by the union of peduncles, but it may originate from one of the peduncles at a point near the axil. Bracts formed at the axil of pedicels often have a reddish tinge. A reddish tinge is also present on many pedicels near the calyx. Hair on the pedicels 20 mm. below tertiary flowers lays irregularly parallel with the pedicel.

Flowers are abundant and are visible above the plant. Flowers average mainly 7 petals per flower. Anthers produce an abundance of pollen even under wet cold condition.

*Fruit*

Crown crop berries are generally large and of high quality when plants are vigorous. Subsequent crop fruit size is medium to large in size, but secondary and tertiary may be considerably smaller. Primaries are mainly 35 to 45 mm. in length with width generally smaller than length. Production is comparatively uniform both first and second year during spring, summer and fall crops. Fruit shape is generally medium wedge to medium conic in outline. Shoulders are rounded at the calyx and are not necked. Epidermis and flesh are firm with a small to medium core cavity. The fruit surface of primaries, secondaries and tertiaries is firm and except for exerted seed is uniformly smooth, only rarely malformed, with a high gloss and have a uniform spacing of the seed. All seeds normally become fertilized and are medium to large and are exerted. Seed generally remains yellow, but will darken when exposed to sunlight. Fruit has a medium to good dessert quality. The fruit surface is Carmine, Plate No. I and the color of flesh near the fruit surface is Scarlet Red, Plate No. I.

*Calyx*

Large in diameter with primaries during mid-summer averaging 35 to 45 mm. in diameter. Sepals are large and overlap, and are abundant. Individual sepals may be as large as 10 mm. in width and 25 mm. long. Serrations are usually present in sepals. The calyx may be held equal to the fruit surface or in a reflexed position. Color of sepals on side facing the fruit is Empire Green, Plate No. XXXII.

I claim:

1. The new and distinct variety of strawberry plant herein described and illustrated, and identified by the characteristics enumerated above.

No references cited.

ROBERT E. BAGWILL, Primary Examiner